United States Patent [19]
Wilson et al.

[11] Patent Number: 5,447,512
[45] Date of Patent: Sep. 5, 1995

[54] CONTROLLER FOR INTRACORPOREAL KNOT TYING APPARATUS

[75] Inventors: Jeff A. Wilson, Mendon, Mass.; V. John Ragnato, Hattiesburg, Miss.

[73] Assignee: Boston Scientific Corporation, Natick, Mass.

[21] Appl. No.: 146,884

[22] Filed: Nov. 2, 1993

Related U.S. Application Data

[63] Continuation-in-part of Ser. No. 903,022, Jun. 23, 1992, Pat. No. 5,281,236.

[51] Int. Cl.⁶ ............................................. A61B 17/04
[52] U.S. Cl. ............................. 606/139; 606/148; 604/281; 289/17
[58] Field of Search ............... 606/139, 148; 604/281, 604/284; 289/17, 2

[56] References Cited

U.S. PATENT DOCUMENTS

| | | | |
|---|---|---|---|
| 3,580,256 | 5/1971 | Wilkinson | 606/232 |
| 4,351,333 | 9/1982 | Lazarus et al. | 604/164 |
| 4,641,652 | 2/1987 | Hutterer et al. | . |
| 4,747,840 | 5/1988 | Ladika et al. | 604/281 |
| 4,874,360 | 10/1989 | Goldberg et al. | 604/281 |
| 4,913,683 | 4/1990 | Gregory | 604/281 |
| 4,950,285 | 8/1990 | Wilk | 606/232 |
| 4,957,498 | 9/1990 | Caspari et al. | 606/146 |
| 4,961,741 | 10/1990 | Hayhurst | 606/139 |
| 4,986,814 | 1/1991 | Burney et al. | 604/281 |
| 5,087,263 | 2/1991 | Li | 606/148 |
| 5,098,137 | 3/1992 | Wardall | 289/17 |
| 5,100,418 | 3/1992 | Yoon et al. | 606/139 |
| 5,100,421 | 3/1992 | Christoudias | 606/147 |

OTHER PUBLICATIONS

Endoscopic Suturing and Knot Tying Manual, Ethicon, Inc. 1991.

*Primary Examiner*—Gary Jackson
*Attorney, Agent, or Firm*—Pearson & Pearson

[57] ABSTRACT

A controller for an intracorporeal knot tying device including a hollow handle housing and a slider operator captured in the handle for linear motion between proximal and distal positions. The slider attaches to an elongated, tubular member formed of a shape memory material for carrying a suture thread through an internal passage and a bight formed in the tube. An outer sheath extends from the handle and supports the remaining length of the tube. When a knot is to be formed, a free end of the suture is pulled through tubular member by means of an introducer. A physician advances the operator to displace the distal end of the tubular member to form the bight. Subsequently, the physician retracts the operator to a proximal position to straighten the bight and throw off a knot in the suture thread for subsequent tightening. The operator includes means for grasping the suture.

20 Claims, 13 Drawing Sheets

CONTROLLER FOR INTRACORPOREAL KNOT TYING APPARATUS

CROSS-REFERENCE TO RELATED APPLICATION

This application is a continuation-in-part of our U.S. patent application Ser. No. 07/903,022 filed Jun. 23, 1992, now U.S. Pat. No. 5,281,236, for Method and Device for Intracorporeal Knot Tying.

BACKGROUND OF THE INVENTION

1. Field of the Invention

This invention generally relates to surgical apparatus and procedures and more specifically to a device and method for facilitating intracorporeal knot tying during endoscopic surgical procedures.

2. Description of Related Art

In endoscopic surgical procedures, all the techniques of dissection, cutting, suturing and knot tying must be performed with various elongated instruments that extend through trocars into a cavity of a patient. These instruments include needle holders, tissue graspers, introducers and related instruments for facilitating both extracorporeal and intracorporeal knot tying during endoscopic surgical procedures. Many of these systems utilize preformed loops to form ligatures or needle sutures. However, when preformed loops are used for ligatures, they can only be applied to tissue appendages. They can not, for example, be tied around ducts between two organs. Preformed loops also have a tendency to lock prematurely, that is, before the ligature is finally cinched in place. Extracorporeal knot tying can produce lost insufflation and requires extra time that can extend the overall time for completing a surgical procedure. Transferring a knot from the exterior of the body to the suture site is subject to premature cinching of the knot and the knots are subject to breakage when very thin sutures are used. Intracorporeal knot tying has been difficult to master and is also very time consuming.

The following patents disclose a number of apparatus that have been proposed for facilitating extracorporeal suture tying:

U.S. Pat. Nos. 3,580,256, (1971), Wilkinson 4,961,741, (1990), Hayhurst 4,957,498, (1990), Caspari et al 5,087,263, (1992), Li 5,098,137, (1992), Wardall The Wilkinson patent discloses apparatus that supports a suture in an overlapping loop formation so one end of a suture can be threaded through the loop to form a throw and when pulled tight, a knot. However, in the Wilkinson patent the suture loop must be encased in wax prior to the surgical procedure and a separate casing or structure must be formed independently for each knot.

The Hayhurst patent discloses apparatus in which leading and trailing members guide a pair of suture knots, such as overhand knots, to a tissue surface. The first overhand knot is secured against the tissue as the second knot advances.

The Caspari et al patent disclose a suturing instrument that enables an extracorporeally tied knot to be moved into the body. The apparatus uses a throw stick to advance a knot to the tissue through a cannula.

The Li patent discloses a suture throw holder and rundown system. This apparatus includes a shaft with a cavity and longitudinal and radial slots for receiving a knot and extensions of a suture.

The Wardall patent discloses a structure for forming a knot, extracorporeally. It comprises a fork-like device with first and second tines.

The following patents disclose other proposals for suturing tissue:

U.S. Pat. Nos. 4,950,285, (1990), Wilk 5,100,418, (1992), Yoon et al 5,100,421, (1992), Christoudias The Wilk patent discloses a specially formed suture having at one end a preformed loop, a specially formed adjacent surface and a special capture structure.

The Yoon et al patent discloses a suture tie and applicator which holds preformed suture ties comprising rigid or semi-rigid segments of sutures disposed within and extending out of the distal end of a tubular locking member. The locking member displaces along the tie until it closes the open side of a tissue receiving area.

The Christoudias patent discloses a suture assembly that includes a needle holder, needle transporter and a needle suture.

None of the foregoing references disclose apparatus that enables or can be adapted to enable a surgeon to tie knots intracorporeally. Consequently a typical intracorporeal knot tying method involves wrapping one free end of a suture thread into a series of loops around a needle holder proximate a tissue site. Then the surgeon uses a grasping instrument to remove the loops from the needle holder without dropping a loop. Next the surgeon picks up the other free end of the suture thread through the loops. Finally the surgeon manipulates both ends of the suture tie to advance the resulting knot toward the tissue and to tighten the knot. Then, as this is a form of slip knot, the procedure is repeated.

As will be apparent, this process is time consuming and complex. It requires great dexterity by the surgeon and is difficult to master. Various instruments must be withdrawn after the suture has passed through the tissue and this further complicates the procedure. Moreover, each time an instrument is replaced, any gas being used in conjunction with the procedure can escape through an open trocar. Notwithstanding these problems, surgeons continue to use either of these extracorporeal or intracorporeal knot tying procedures.

SUMMARY

Therefore it is an object of this invention to provide a new method and device for facilitating intracorporeal suture tying.

Still another object of this invention is to provide a new method and device for facilitating intracorporeal suture tying that is adapted for producing multiple knots in situ.

Still another object of this invention is to provide a new method and device for facilitating intracorporeal suture tying in locations with limited access.

Yet another object of this invention is to provide a new method and device for facilitating intracorporeal suture tying that minimizes the difficulty of and the time required for tying such intracorporeal suture knots.

Still yet another object of this invention is to provide an improved controller for an intracorporeal suture tying device.

Yet still another object of this invention is to provide an improved controller for an intracorporeal suture tying device that can be operated with one hand.

In accordance with this invention, a device for facilitating a tying of an intracorporeal suture includes an elongated flexible tube formed of a shape memory material. The tube is formed with a bight at the distal end and carries the suture thread. An elongated sheath overlies the elongated flexible tube for straightening the bight. A knot is formed by drawing a free end of the suture through a loop formed by the bight and then straightening the bight to produce a knot in the suture thread. A controller for operating the device includes a first and second elements attached to the proximal ends of the elongated flexible tube and elongated sheath. The two elements move relative to each other thereby to control the relative positions of the elongated flexible tube and sheath with respect to each other.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF THE ILLUSTRATIVE EMBODIMENTS

Figure 1:
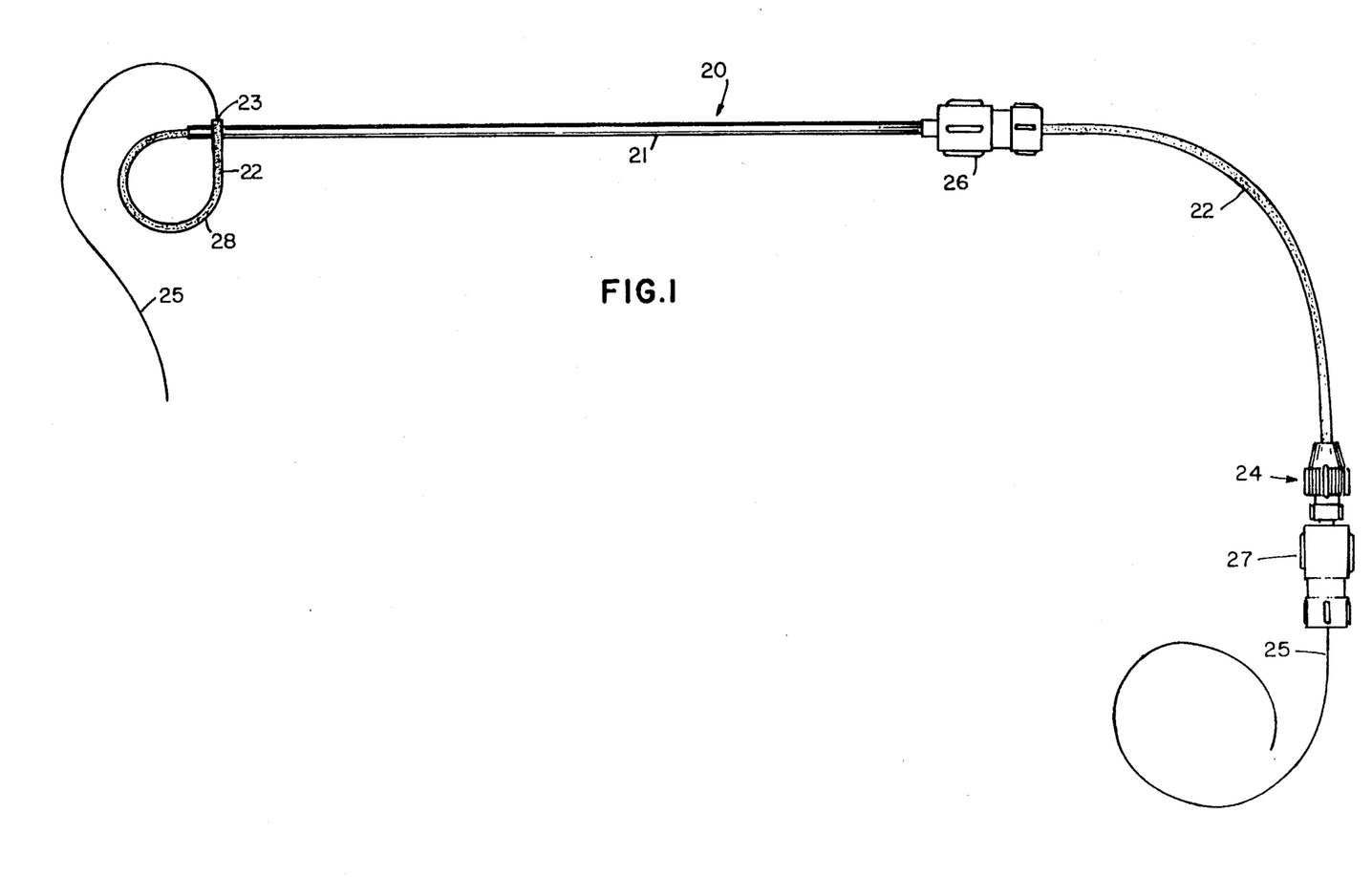
FIG. 1 is a plan view of a suture tying device constructed in accordance with this invention particularly adapted for tying ligature sutures.

FIG. 1 discloses a intracorporeal knot tying device 20 constructed in accordance with this invention that comprises sheath 21 and an elongated tube or catheter 22. The catheter 22 has a distal end 23 and a proximal end 24. The catheter 22 carries a suture thread 25.

The proximal end of the sheath 21 terminates with a Leur lock fitting 26 while the proximal end 24 of the catheter 22 terminates in a Leur lock fitting 27 in this particular embodiment. The Leur lock fittings 26 and 27 provide structure for manipulating the position of the sheath 21 and catheter 22 with respect to a particular intracorporeal site or with each other.

As apparent from FIG. 1, the sheath 21 supports only a portion of the catheter. The catheter 22 slides freely within the sheath 21 whenever the Leur lock fitting 26 is released. Similarly the suture thread 25 slides freely within the catheter 22 when the Leur lock fitting 27 is released.

The catheter 22 is formed of a composition having shape memory so the distal portion of the catheter 22 can be formed into and retain the position of a bight 28. More specifically, the distal end portion 23 of the catheter 22 is bent by substantially 270° and partially crosses an intermediate portion of the sheath 21.

A number of compositions have shaped memories. Spring steel and nitinol are examples of metals with shape memory. Polyethylene and polypropylene are examples of plastic materials having shape memory. Percuflex ® materials available from the assignee of the present invention and C-flex ® materials available through Concept Business Polymers are specific examples of such plastic materials. The catheter 22 may also comprise a composite of plastic and metals such that the overall composite has shape memory.

Thus, the catheter 22 can not be composed of any material that has shape memory and that allows bight 28 to be straightened under a reasonable force and then to return to the form of the bight 28 when the external force is released. The composition also should be compatible with a medical environment.

The intracorporeal knot tying device 20 constructed as shown in FIG. 1 enables a physician to release the Leur lock fitting 26 and advance the sheath 21 distally over the catheter 22 and straighten the catheter 22 at the bight 28. If the sheath 21 moves proximally with respect to the catheter 22, the distal end 23 emerges from the sheath 21 and reforms the bight 28 shown in FIG. 1.

Figure 2:
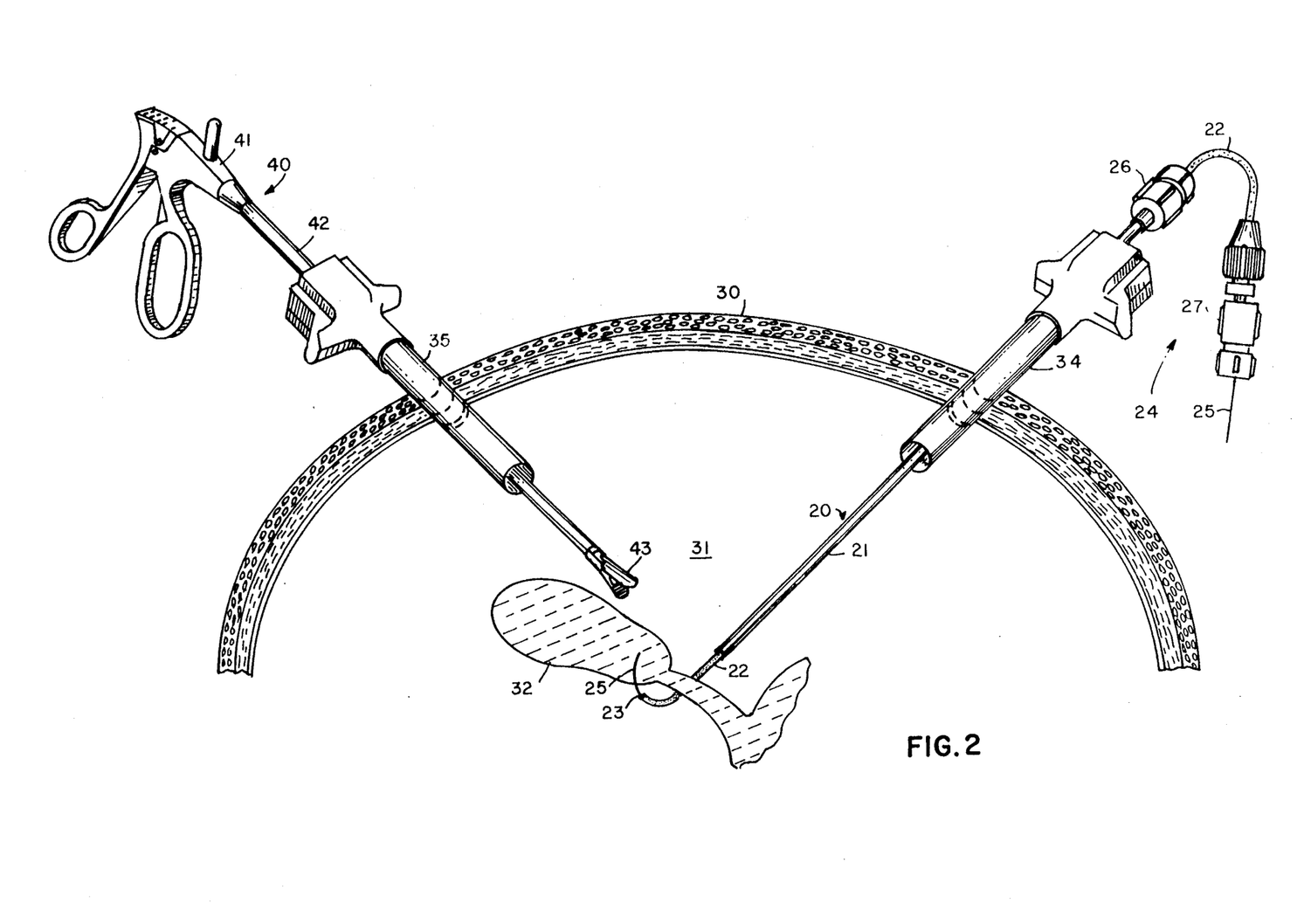
FIG. 2 is a schematic view that is useful in understanding the operation of this invention.

FIG. 2 discloses, in schematic form, an application of the knot tying device 20 for use with a ligature. For purposes of explanation, FIG. 2 depicts a human torso 30 and an internal cavity 31 surrounding a gall bladder 32 and cystic duct 33. A trocar 34 carries the device 20 including the sheath 21, the catheter 22 and suture thread 25. Another trocar 35 penetrates the torso 30 to provide an access for a grasper 40 having a handle 41, an intermediate shaft 42 and grasper jaws 43 at the distal end thereof. Although not shown in this particular embodiment, a surgeon would view the cavity 31 through an endoscope placed proximate the cavity 31 through another access port.

In FIG. 2, the sheath 21 is positioned along the catheter 22 toward the distal end 23 thereby to straighten the catheter 22 partially. This opens the bight 28 (shown in FIG. 1) and allows a physician to manipulate the device 20 and to position the suture thread 25 on one side of the portion to be ligatured, in this particular example the cystic duct 33. The physician then can utilize the grasper 40 and capture the suture thread 25 with the jaws 43 to hold the distal end of the suture thread 25 in a stable position. If the physician then releases the Leur lock fitting and withdraws both the sheath 21 and the catheter 22 proximally, the suture thread 25 pull from the distal end 23. If, after the distal end 23 is clear of the cystic duct 33, the physician further retracts the sheath 21 with respect to the catheter 22, the catheter 22 will reform the bight 28 as shown in FIG. 3.

Figure 3:
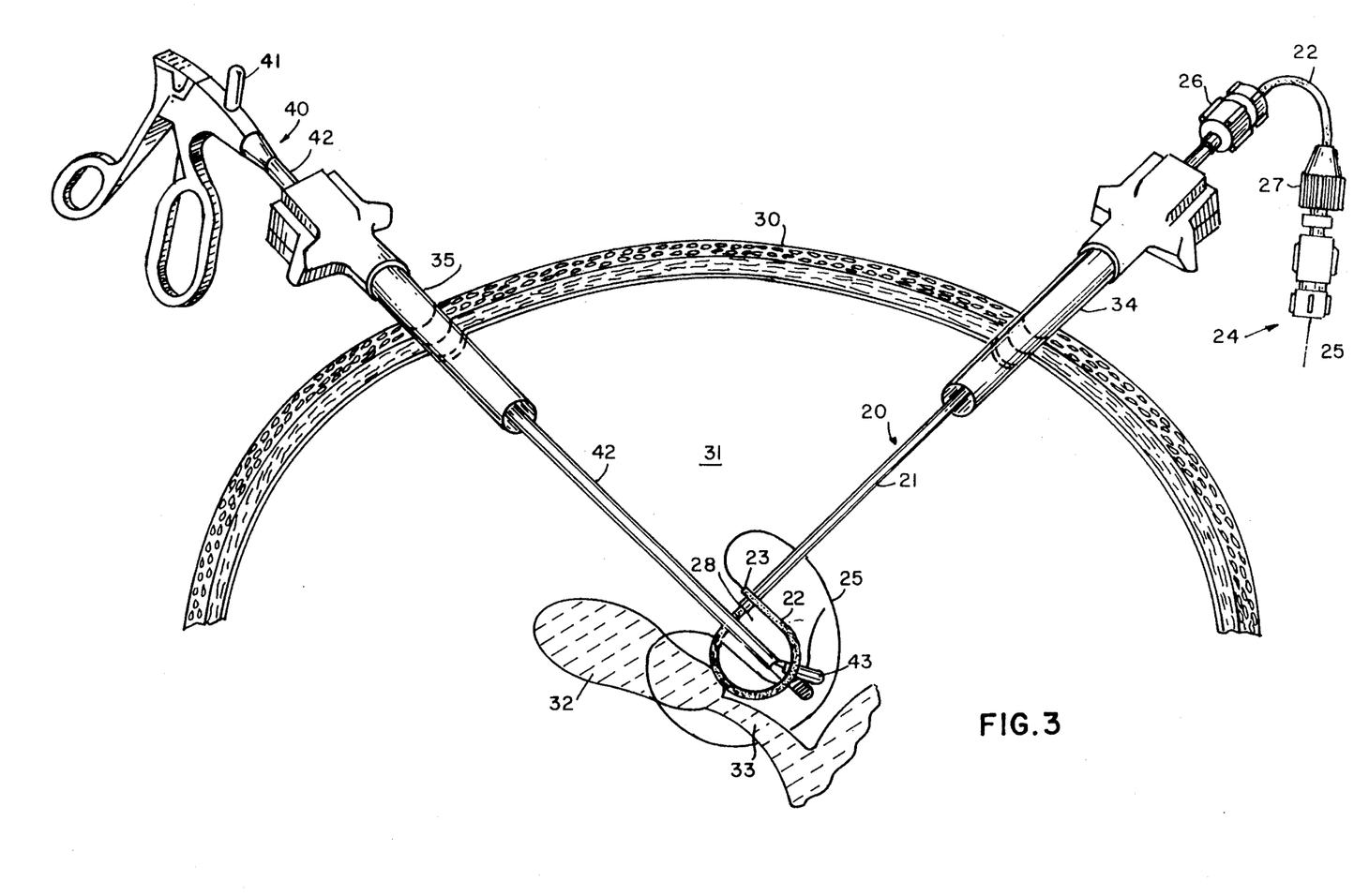
FIG. 3 is another schematic view that is helpful in understanding this invention.

More specifically, in FIG. 3 depicts the relationship of the various instruments at a next stage in the procedure. The physician has subsequently extended the grasper 40 and led the end of the suture thread 25 through the bight 28. Next the physician will release the end of the suture thread 25, partially withdraw the grasper 41 and then extend it to grasp the end of the suture thread 25 on the other side of the bight 28. In other circumstances it may be possible to form the ligature by extending the grasping jaws 43 through the bight 28, grasping the end of the suture thread 25 and retracting the jaws 43 back through the bight 28 to complete a loop.

Figure 4A:
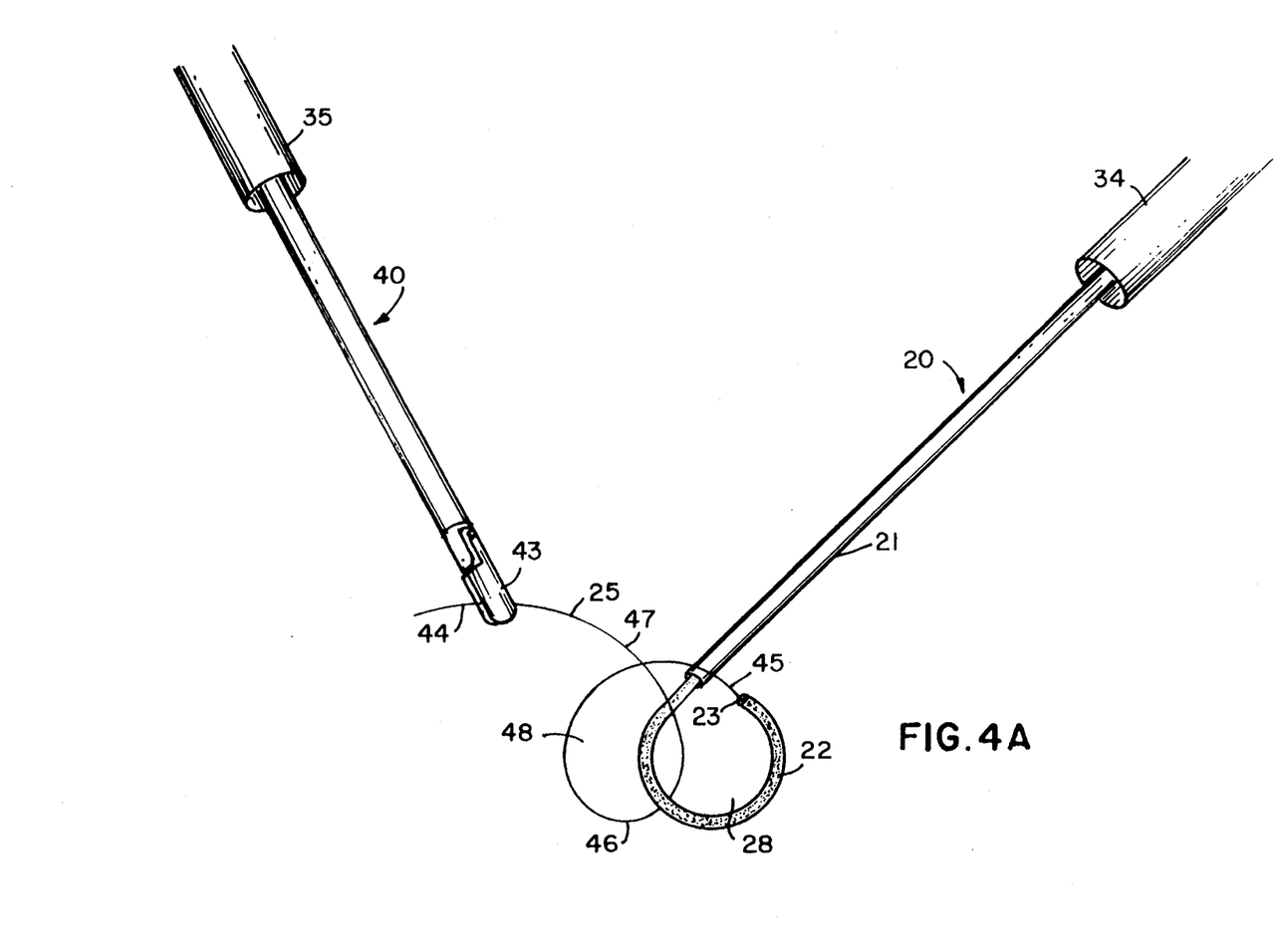
FIGS. 4A through 4E depict a method for using the device shown in FIGS. 1 through 3.

When the physician completes the specific operations in FIGS. 2 and 3 or other similar operations, the device 20, suture 25 and grasping jaws 43 can produce a configuration as shown by the simplified view in FIG. 4A. The grasping jaws 43 on the grasper 40 clamp a distal end 44 of the suture thread 25. A portion 45 of the suture thread 25 extends from the distal end 23 of the catheter 22 and overlies the sheath 21. An adjacent portion 46 passes through the bight 28; and a final portion 47 overlies the section 46. Sections 46 and 47 therefore form a hitch or loop 49 around the catheter 22.

Figure 4B:
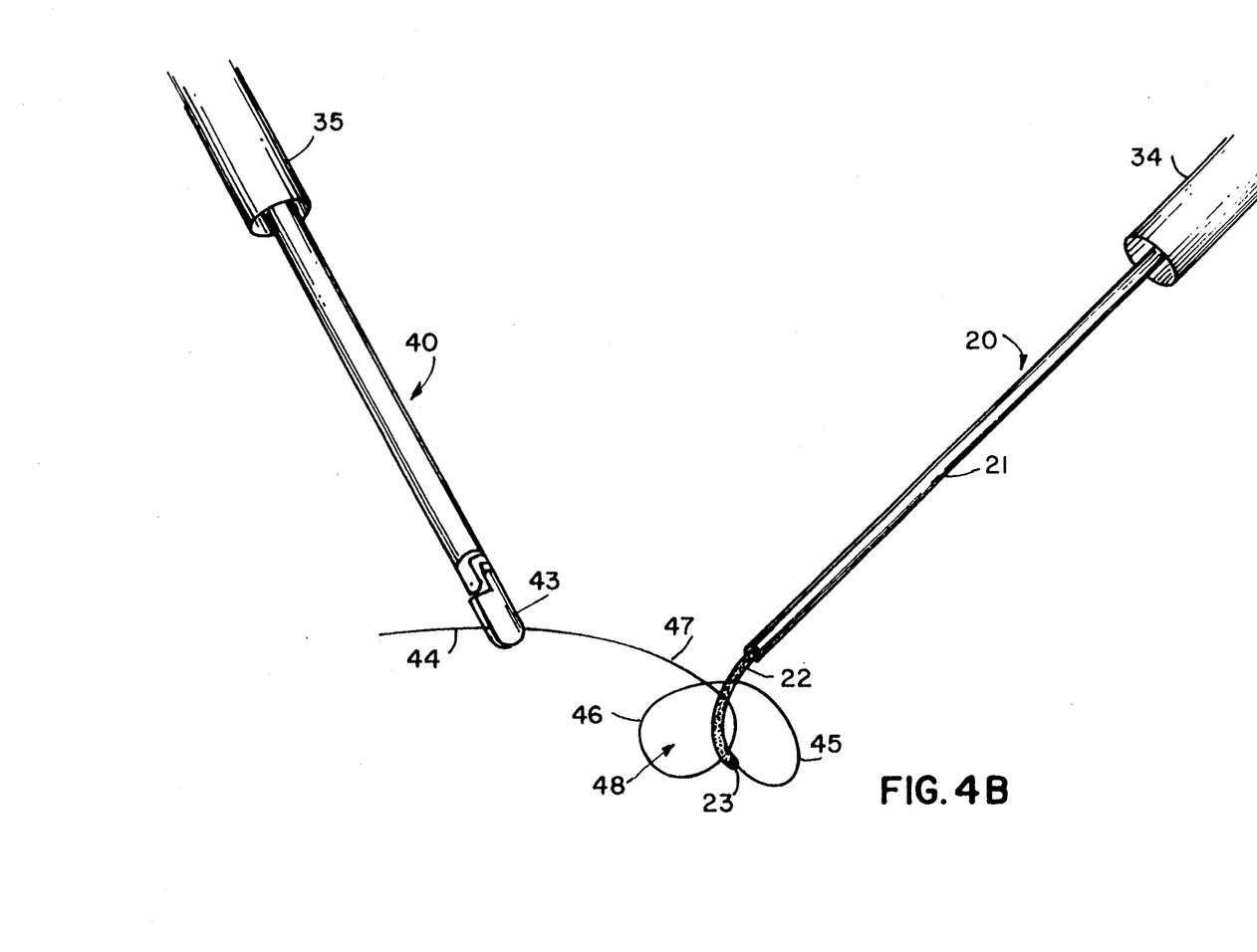
Figure 4C:
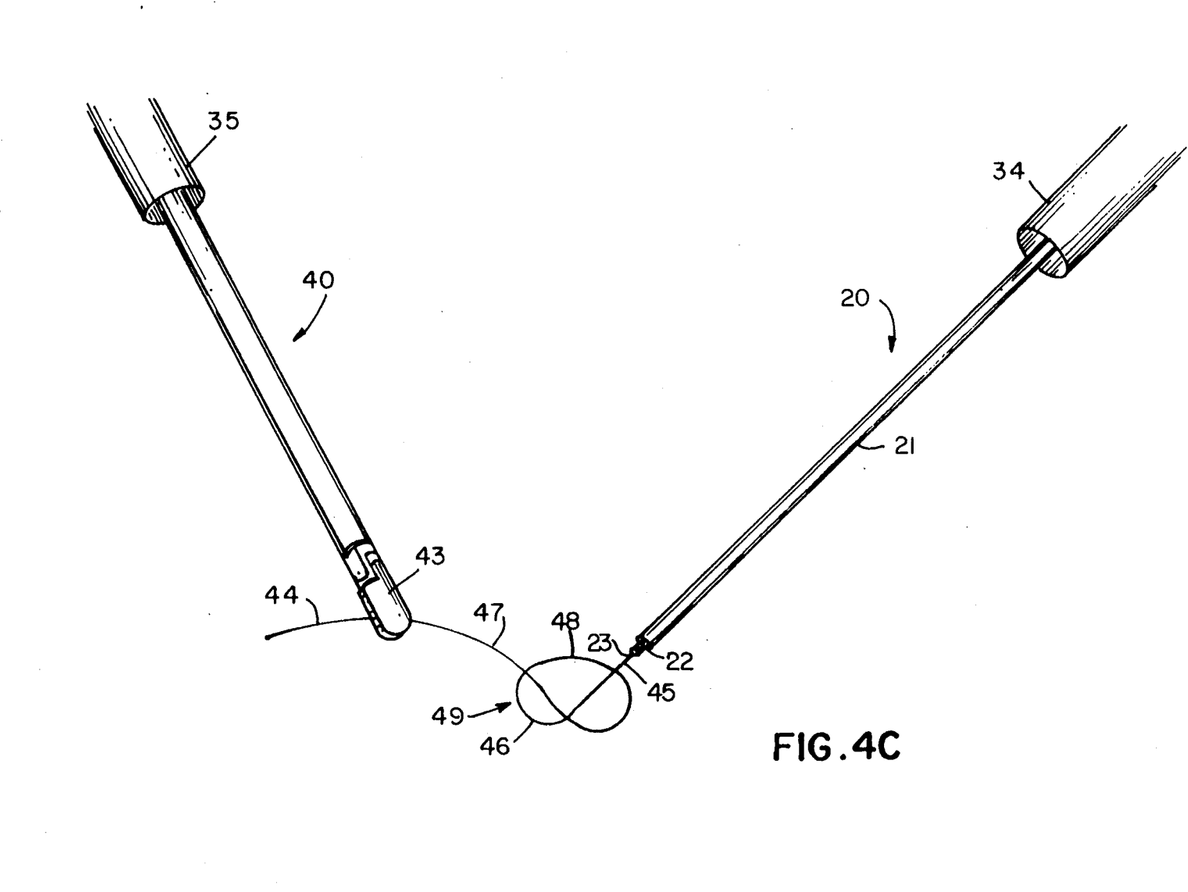

Referring to FIG. 4B, the surgeon holds the distal end 44 of the unit in place with the grasper 40 and withdraws the catheter into the sheath 21 along with the suture thread 25. Thereupon the portion 45 draws through the loop 48 to produce a knot 49 in the suture 25 as shown in FIG. 4C. Further manipulation of the device 20 and the grasper 40 allows the knot 49 to tighten the loop 48 around a vessel such as the duct 33 in FIG. 3. From this it will be obvious that the vessel need not be an appendage as would be required if a preloop were formed and transferred along an introducer to the site.

Figure 4D:
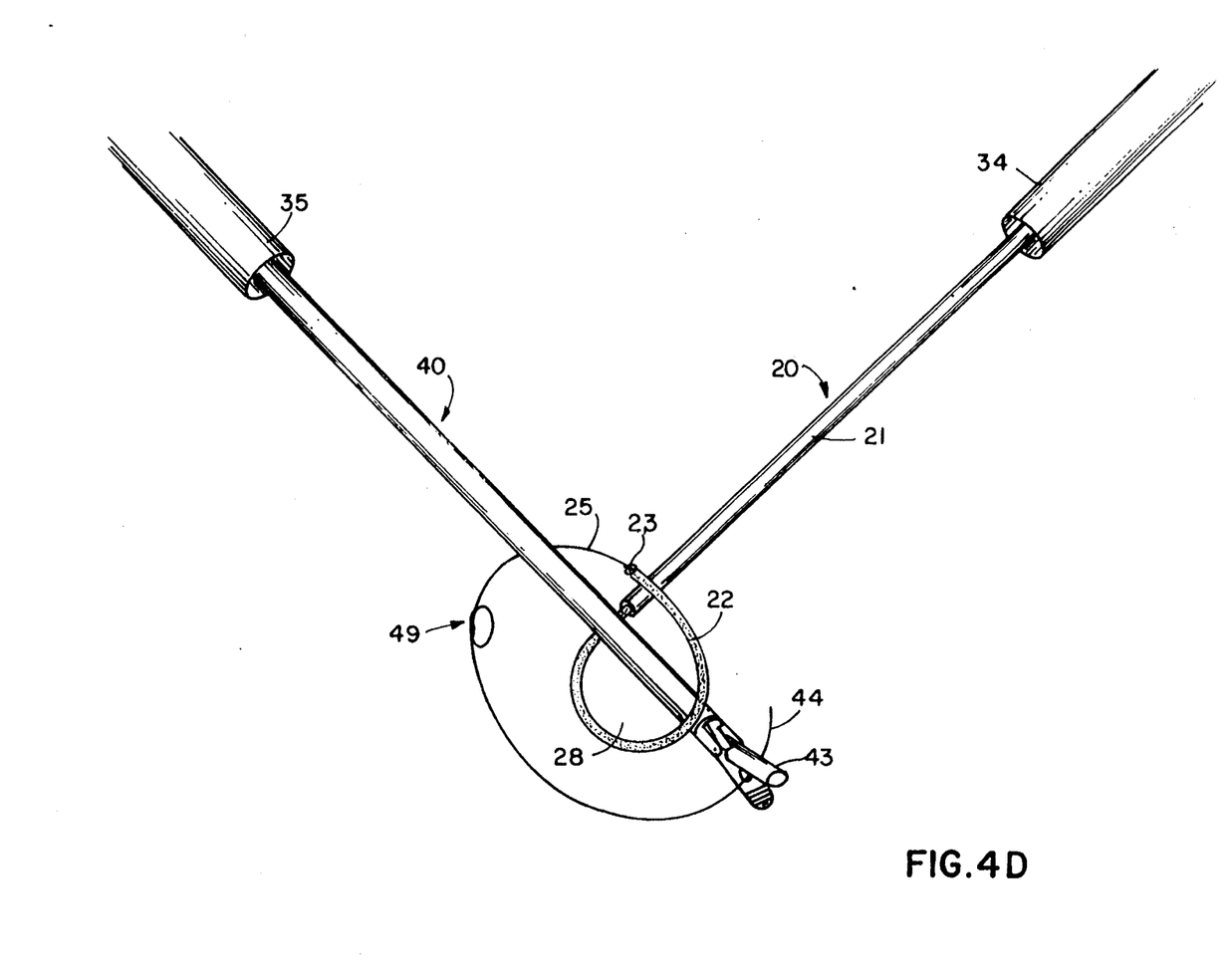
Figure 4E:
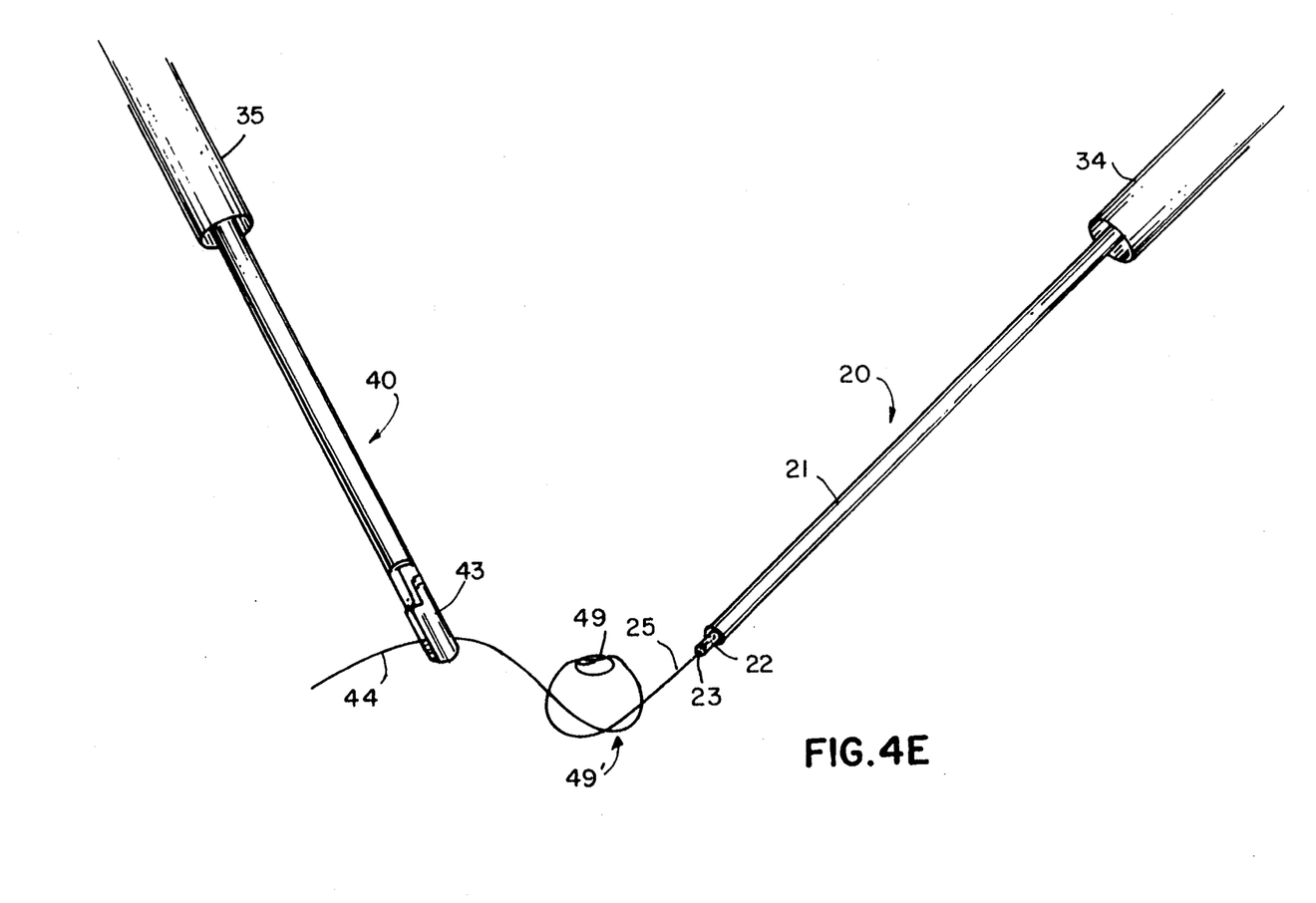

Moreover, once a first overhand knot is formed, the system facilitates the formation of a second knot as shown in FIGS. 4D and 4E. Referring specifically to FIG. 4D, the physician extends the catheter 22 distally to reform the bight 28. This occurs because the catheter 22 has shape memory. Next the physician moves the grasper 40 to reposition the free end 44 of the suture thread 25 in line with the bight 28. Then the physician releases the grasping jaws 40 and extends them through the bight 28. The physician again grasps the free end 44 of the suture 25 in the jaws 43 and pulls the free end through the bight 28.

Referring to FIG. 4E, the physician completes the knot by holding the distal end 44 of the suture 25 in a stable position with the grasper 40. Next the sheath 21 advances distally to straighten the bight 28 and throw off another knot, in this case another overhand knot 49'. When the knots 49 and 49' tighten, they form a square knot.

It has been found that the intracorporeal knot tying device 20 minimizes the tension applied to the suture thread 25. Consequently, the device 20 shown in FIG. 1 enables fine suture threads, in the order of 1 mm or so, sutures to be manipulated without breakage. It is also possible to construct such a device with a minimal outer diameter thereby to facilitate its use with trocars of minimal diameter.

Therefore in accordance with several objects of this invention, the intracorporeal knot tying device 20 provides an apparatus for facilitating the intracorporeal knotting of ligatures. This device and method are particularly adapted for use in areas of limited access because only limited lateral motion of the device 21 is required. All other motion generally occurs along the entrance axis for the device 20 that the trocar 34 establishes. Minimal motions are required of the grasping handle 40.

Furthermore, it has been found that this method is readily learned. Physicians can tie knots more rapidly than was possible with prior devices or procedures. Finally, as shown in FIGS. 4A through 4E, it is possible to use this device intracorporeally to form multiple overhand knots at a single site. Other knots can also be tied.

Figure 5:
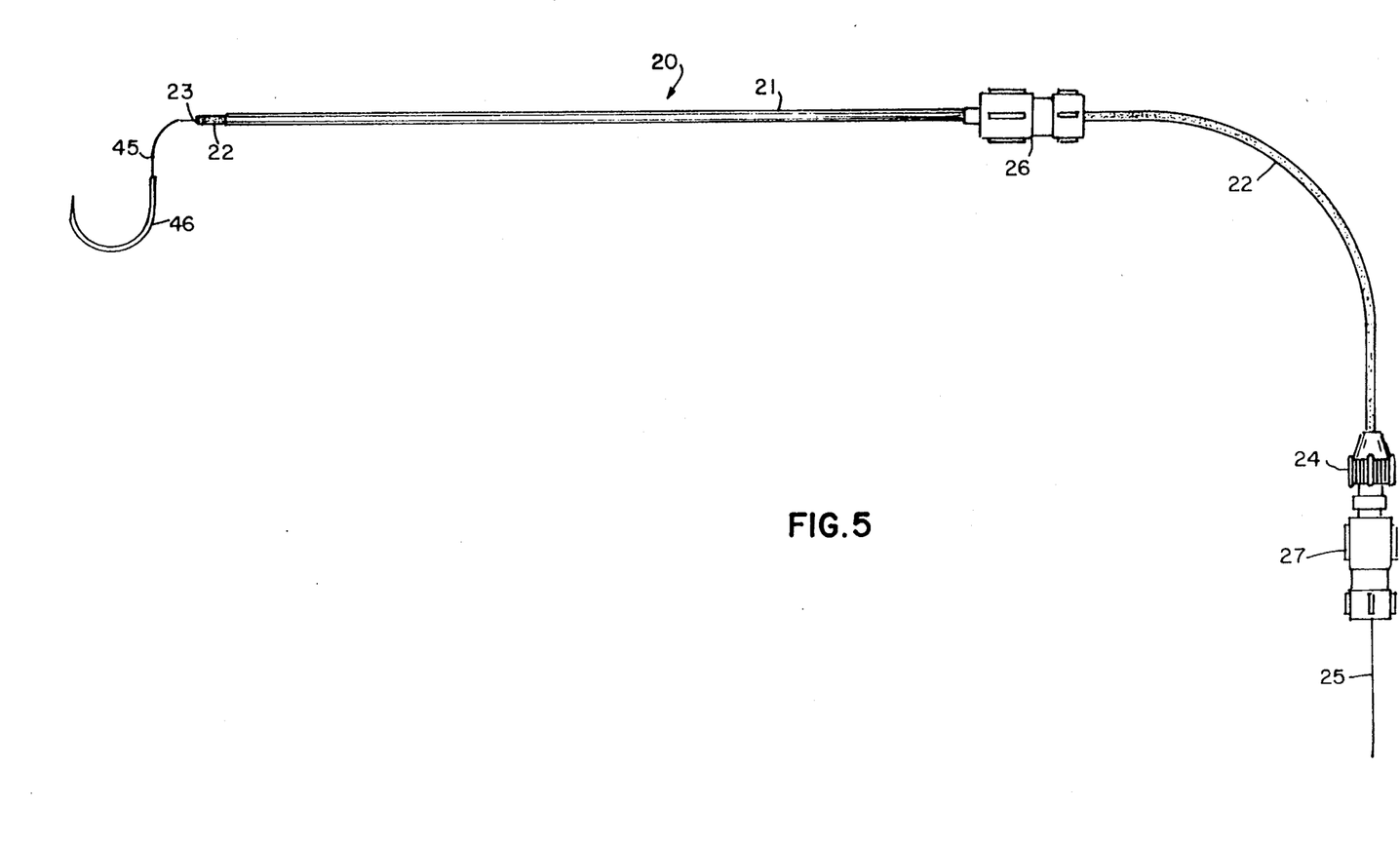
FIG. 5 is a plan view of a suture tying device constructed in accordance with this invention and adapted for use with a needle suture.

This apparatus is also useful with needle sutures such as shown in FIG. 5 where like numbers refer to like elements of the intracorporeal knot tying device 20 shown in FIG. 1. In the embodiment in FIG. 5, the suture comprises a suture thread 50 and a needle 51 at the distal end. The suture thread 50 extends through the catheter 22 in the device 20 and rides in a sheath 21. Leur lock fittings 26 and 27 at the proximal end of the device 20 provide means for stabilizing the system and provide a means for manipulating the device 20 in the same manner as was described with respect to FIG. 1.

Figure 6:
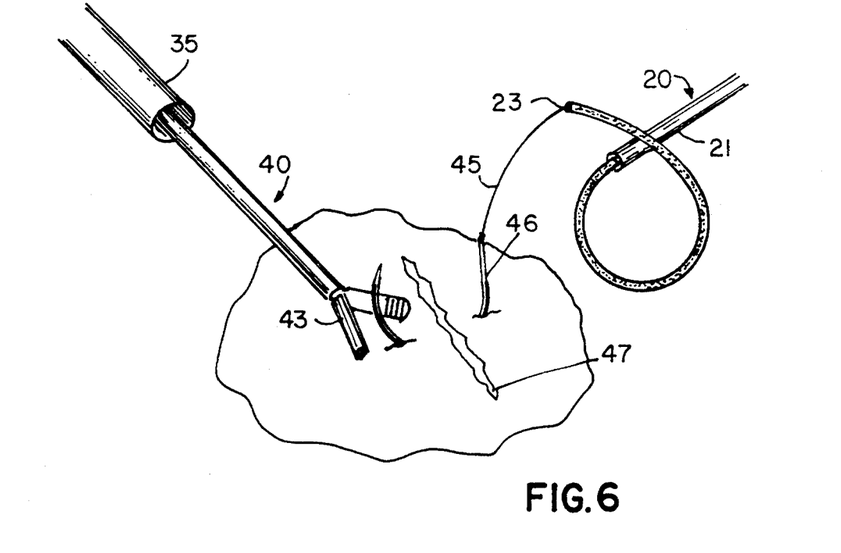
FIG. 6 depicts in schematic form, one aspect of the operation of the device in FIG. 5.

FIG. 6 depicts a suture 50 that joins two pieces of tissue 52 separated along a tear 53. Specifically the physician uses the grasper 40 to lock the jaws 43 onto the curved needle 51 and penetrate the tissue 52 in an arcuate path spanning the tear 53. As shown in FIG. 6 the physician can grasp the end of the needle 51 in the jaws 43 and pull the needle 51 through the tissue 52 carrying the suture thread 50. When a sufficient amount of suture thread 50 has been pulled past the tear 53, the needle 51 is laid on the tissue 52.

Figure 7:
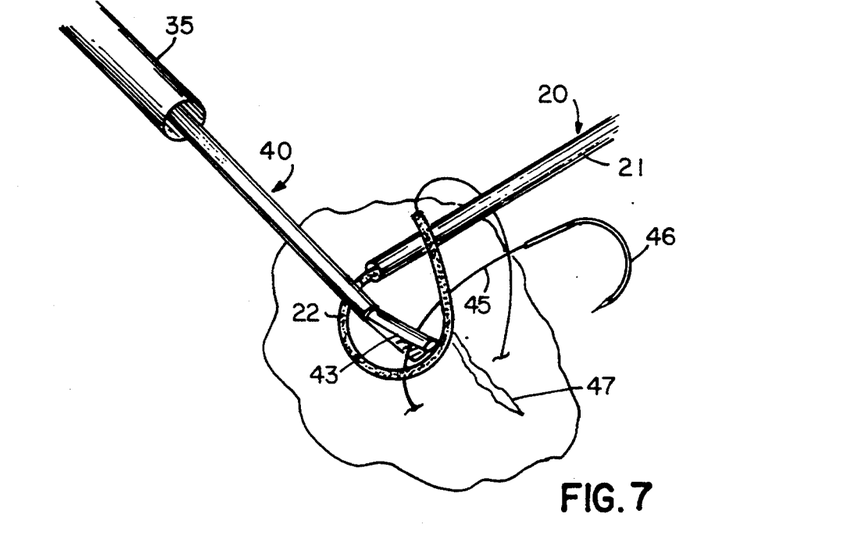
FIG. 7 illustrates another aspect of the operation of the device in FIG. 5.

As shown in FIG. 7, the physician redirects the grasping jaws 43 through the bight 28 formed by the catheter 22 to grasp the needle 51 or the suture thread 50 adjacent the needle 51. The physician withdraws the needle 51 and adjacent thread 50 through the bight 28 to form a loop or hitch around the catheter 21. Thereafter the physician can proceed with a method as shown in FIGS. 4A through 4E to produce one or more overhand or other knots at the tear 53.

Figure 8:
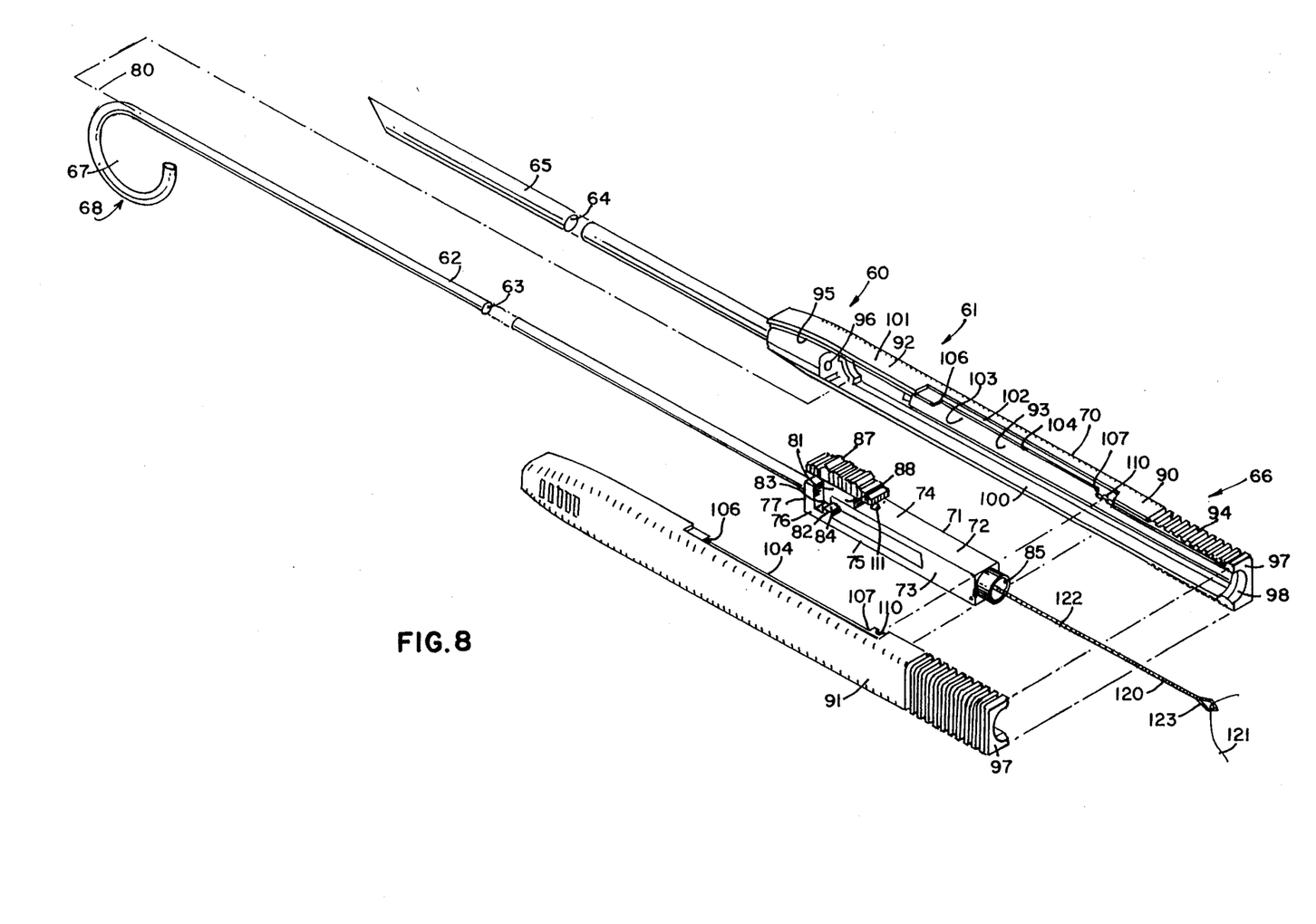
FIG. 8 is an exploded view of an intracorporeal knot tying device of the type shown in FIGS. 1 through 7 with an improved controller that embodies this invention.
Figure 9:
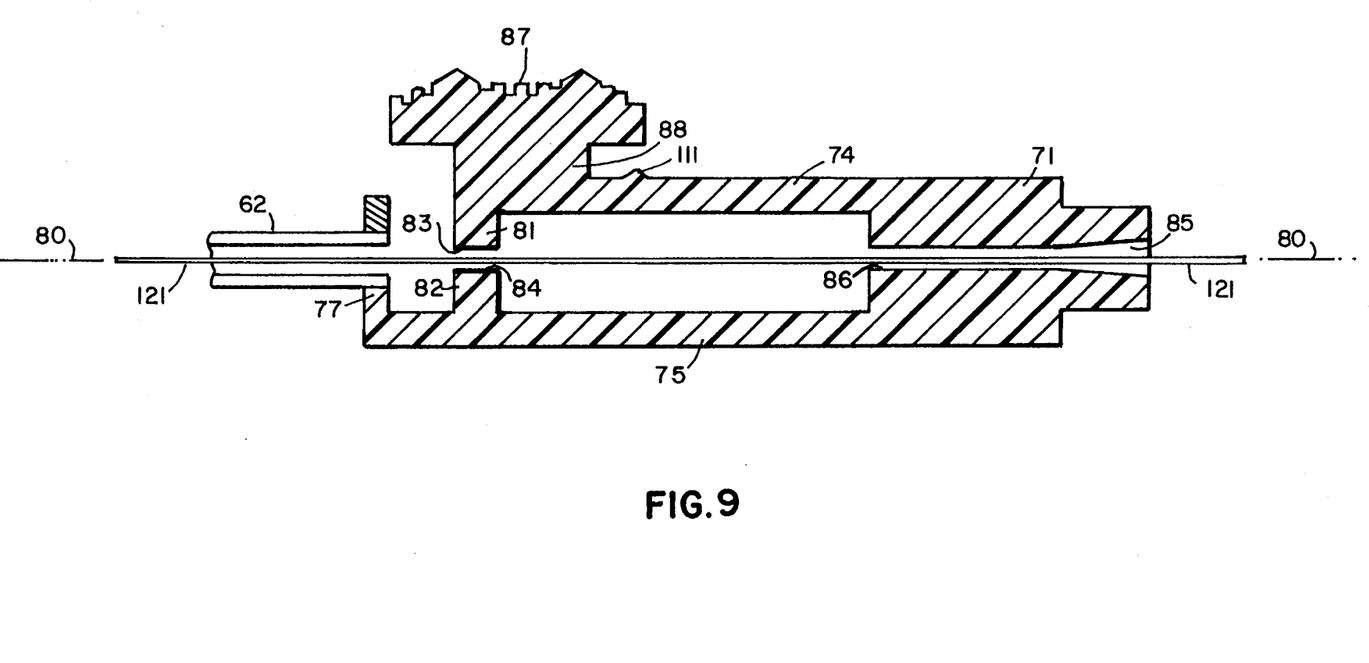
FIG. 9 is a detailed cross-section of a portion of the controller shown in FIG. 8.
Figure 10:
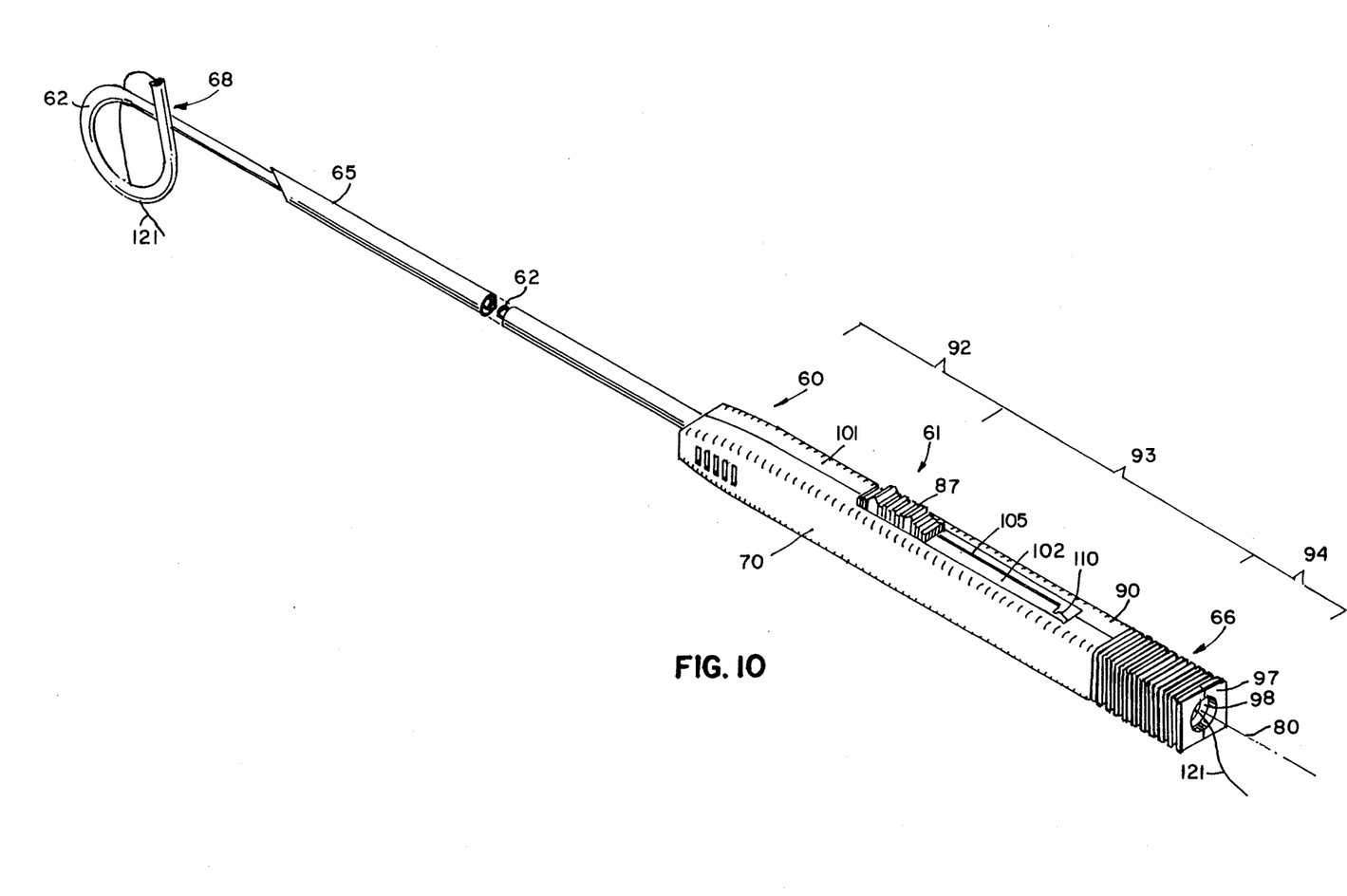
FIG. 10 is a perspective view of the device shown in FIG. 8 with the controller in an assembled form.

FIGS. 8 through 10 disclose an alternative embodiment of a device 60 with a controller 61 at a proximal end that facilitates knot tying. As with the device in FIGS. 1 through 7, the device 60 includes an elongated flexible tube 62 formed of a shape memory material having a lumen 63 extending through its length. The tube 62 extends through a lumen 64 in an elongated linear sheath 65. The controller 61 attaches to the elongated tube 62 and sheath 65 at a proximal end 66 of the device 60. When the tube 62 is not constrained by the sheath, it forms a loop or bite 67 at a distal end 68.

As most clearly is shown in FIGS. 8 and 9, the controller 61 includes a handle housing 70 that attaches to the sheath 65 and a slider or operator 71 that attaches to the proximal end of the elongated tube 62. The operator 71 includes a base 72 with sliding surfaces 73. A first arm 74 and a second arm 75 extend distally from the base 72. The second arm 75 includes a distal extension 76 that supports a transverse leg 77 distally beyond the termination of the first arm 74 and transverse to an axis 80 through the device 60.

The arms 74 and 75 also include transversely extending, oppositely facing legs 81 and 82 that terminate in counterfacing clamping surfaces 83 and 84. The arms 74 and 75, being cantilevered from the base 72, can deflect toward each other and clamp any suture or other structure passing through the operator 70 between the clamping surfaces 83 and 84.

The operator 71 additionally includes a proximally located aperture 85 at one end of a passage 86 through the base 72. A thumb pad 87 connects to the arms 74 by means of a connector portion 88. The thumb pad 87 provides a simple control element by which a physician slides the operator 70 inside the housing 70 along the axis 80 and deflects the arm 74 toward the arm 75.

The housing 70 in this particular embodiment includes counterfacing members 90 and 91 organized axially into a distal section 92, central section 93 and proximal section 94. A fitting 95 in the distal section 92 of the member 90 is banded to the elongated sheath 65, and an axial passage 96 through the connector portion 95 aligns with the lumen 64 in the sheath 65. The proximal section 94 terminates with a transverse end surface 97 with a central aperture 98. This aperture 98 is coaxial with the axis 80.

The central section 93 has a bottom slide surface 100 over which the exterior surface of the base portion 72 and second arm 75 can slide. A top surface 101 provides an interior sliding surface for the base portion 72 and the arm 74. The top surface 101 also includes an axially extending recessed surface 102. A surface 103 formed on the interior of the first member 90 of the housing and a corresponding surface formed in the second member 91 of the housing 70 provide additional sliding surfaces for positioning the operator 71. Consequently when the first and second members 90 and 91 are assembled, they capture the operator 71 so it can only reciprocate along the axis 80.

Slot portions 104 formed at the recessed surfaces 102 of each of the members 90 and 91 are coextensive with the central portion 93. When the members 90 and 91 are assembled, a resulting slot 105 allows the connector 88 between the arm 74 and the thumb pad 87 to slide into slot 104. The slot 105 terminates at a distal edge 106 and a proximal edge 107 that define distal and proximal limits on the motion of the operator 71 by engaging vertical surfaces on the connector 87.

In use, a physician can lock the operator 71 in a proximal position by means of a detent mechanism including an aperture 110 formed through the members 90 and 91 and a detent 111 centrally disposed on the arms 74 adjacent the connector 87. When a physician retracts the thumb pad 87 to a full proximal position, the detent 111 engages the aperture 110, normally with a minimal spacing between the edge 115 and the connector 88.

FIG. 8 depicts an introducer 120 that can be used to thread a suture 121 into the knot-tying device 60. The introducer will be formed of a coiled spring or wire body 122 with an eye 123 at one end. In use a physician would retract the thumb pad 87 to a proximal locked position where the detent 111 engages the aperture 110. This retracts the elongated tube 62 into the sheath 65 and removes the bight 67. The introducer 120 is then fed through the lumen 63 from the distal end 68 with the eye 123 in a leading position. The eye 123 is shaped to lead the introducer 120 from the lumen 63 between the clamping surfaces 83 and 84 and through the passage 86 to exit through the end 97 of the handle 70 as shown in FIG. 8. After the suture 121 is fed through the eye 123, as shown in FIG. 8, the introducer 120 can be withdrawn from the distal end 68, pulling the suture 121 through the device 60 as shown in FIG. 10.

When the controller 61 is assembled as shown in FIG. 10, axial motion of the thumb pad 86 in the slot 105 moves the elongated tube 62 relative to the sheath 65. In addition, transverse pressure applied to the thumb pad 86 causes the arm 74 to deflect such that the clamping surface 83 moves transversely to the axis 80 and toward the clamping surface 84. When the thumb pad 87 is released, internal forces in the operator 71 return the arm 74 to the sliding surface formed by the tip 101.

After locating the distal end 68 of the device 60 through a trocar, such as the trocar 34 in FIGS. 2 through 4E, the physician engages the thumb pad 87 to deflect it slightly releasing the detent 111 and moving the thumb pad to a distal position whereupon the elongated tube 62 forms the bight 67. After the physician produces the knot as previously described with respect to FIG. 4A, the physician will depress and retract the thumb pad 87 simultaneously. Depressing the thumb pad 87 causes the operator 71 to clamp the suture 121, as most clearly evident from FIG. 9. Consequently both the suture 121 and the elongated tube 82 retract together thereby tightening the knot in the suture 121.

As will now be apparent, the controller 61 facilitates the use of an intracorporeal suture tying device. It is easy to use and readily adapted for one-handed operation. Consequently an intracorporeal knot tying device including a controller constructed in accordance with this invention is particularly adapted for endoscopic surgery and is simple and reliable. Its operation is readily mastered. It can produce a knot tying operation that is significantly faster than previous extracorporeal or intracorporeal procedures. Moreover, the device enables a physician to exercise good control over the knot tying operation with one hand.

Although this invention has been disclosed in terms of certain embodiments including a particular controller embodiment, it will be apparent that many modifications can be made to the disclosed apparatus without departing from the invention. Therefore, it is the intent of the appended claims to cover all such variations and modifications as come within the true spirit and scope of this invention.

What is claimed and desired to be secured by Letters Patent of the United States is:

1. In a device for facilitating the tying of a suture at a distal, intracorporeal location by manipulation at a proximal location including an elongated flexible tube means formed of a shape memory material for supporting a suture between the proximal and distal locations with the tube means being formed with a bight at the distal end and thereby forming a loop in the suture and an elongated sheath means for overlying said tube means, the improvement of control means at the proximal location for controlling the operation of the device, said control means including:

A. first means attached to one of said tube means and said elongated sheath means for controlling the position of the device, and
   B. second means attached to the other of said tube means and said elongated sheath means for controlling the relative positions of said tube means and said elongated sheath means, said second means supported in said first means for selective movement relative to said first means.

2. A device as recited in claim 1 wherein said tube means extends along an axis and wherein said first means includes means for enabling axial displacement of said second means between proximal and distal limits.

3. A device as recited in claim 2 wherein said controller means additionally comprises means for locking said second means at said proximal limit.

4. A device as recited in claim 1 wherein said tube means extends along an axis and wherein said first means includes means for enabling axial displacement of said second means between proximal and distal positions having a spacing corresponding to the relative displacement of said tube means and elongated sheath means for forming the bight when said second means is at one of said proximal and distal positions and for straightening said tube means when said second means is at the other of said positions.

5. A device as recited in claim 1 wherein said tube means extends along an axis and wherein said first means constitutes an axially extending handle housing and said second means comprises a slidable operator and said handle housing includes means for supporting said operator for axial displacement and includes means for establishing proximal and distal limits on the axial displacement of said operator in said handle.

6. A device as recited in claim 5 wherein said limit establishing means includes means for locking said operator at said proximal limit.

7. A device as recited in claim 5 wherein said operator includes means for clamping the suture.

8. A device as recited in claim 1 wherein said tube means extends along an axis and wherein said first means constitutes an axially extending handle housing and said second means comprises a slidable operator and said handle housing includes means for supporting said operator for axial displacement and includes means for establishing proximal and distal limits on the axial displacement of said operator in said handle housing, said proximal and distal limit means being spaced axially within said handle housing by a distance corresponding to the relative displacement of said tube means and elongated sheath means for forming the bight when said operator is at one of said limits and for straightening said tube means when said operator is at the other of said limits.

9. In a device for facilitating the tying of a suture at a distal, intracorporeal location by manipulation at a proximal location including an elongated flexible tube means formed of a shape memory material for supporting a suture between the proximal and distal locations with said tube means being formed with a bight at the distal end and thereby forming a loop in the suture and an elongated sheath means for overlying said tube means, the improvement of controller means at the proximal location for controlling the operation of the device, said controller means including:

A. a handle housing attached to said elongated sheath means for controlling the position of the device, and B. an operator attached to said tube means and supported for movement in said handle housing for controlling the positions of said tube means relative to said elongated sheath means.

10. A device as recited in claim 9 wherein elongated said sheath means and said handle housing extend along an axis and wherein said handle housing includes means for establishing proximal and distal limits for the motion of said operator along the axis.

11. A device as recited in claim 9 wherein said elongated sheath means and said handle housing extend along an axis and wherein said handle housing includes means for establishing proximal and distal limits for the motion of said operator along the axis, the proximal and distal limits being spaced by a distance corresponding to the displacement of said tube means relative to said elongated sheath means for forming the bight when said operator is at said distal limit and for straightening said tube means when said operator is at said proximal limit.

12. A device as recited in claim 9 wherein said tube means extends along an axis and wherein said handle housing and said operator are formed coaxially with said tube axis.

13. A device as recited in claim 12 wherein said tube has a lumen therethrough for receiving the suture and wherein each of said handle housing and said operator have an aperture therethrough at the proximal ends thereof aligned with said tube lumen for enabling the introduction of the suture through the device.

14. A device as recited in claim 13 wherein said handle housing has a first internal cavity formed therein for supporting said operator.

15. A device as recited in claim 14 wherein said handle housing additionally includes a slot extending exteriorly from said first internal cavity and wherein said operator includes a body portion located in said first internal cavity, an operating portion located exteriorly of said handle housing and a connecting portion between said body portion and said operating portion for extending through said slot in said handle housing.

16. A device as recited in claim 15 wherein said handle housing and said operator include complementary locking means for engaging when said operator means is at the proximal limit.

17. A device as recited in claim 15 wherein said operator includes means for clamping the suture.

18. A system for facilitating the tying of a suture at a distal, intracorporeal location by manipulation at a proximal location comprising:

A. an elongated flexible tube means formed of a shape memory material for supporting in a lumen thereof a suture between the proximal and distal locations with said tube means being formed with a bight at the distal end and thereby forming a loop in the suture, B. an elongated sheath means for overlying said tube means, C. controller means at the proximal location for controlling the operation of the device, said controller means including:
 i. handle housing means attached to one of said tube means and said elongated sheath means for controlling the position of the device, and
 ii. operator means attached to the other of said tube means and said elongated sheath means and supported for movement in said handle housing means for controlling the relative positions of said tube means and said elongated sheath means, and D. introducer means for insertion through said tube means lumen and displaceable therethrough for guiding the suture thread into said tube means.

19. A system as recited in claim 18 wherein said handle and said operator means includes complementary locking means for engaging when said operator means is at the proximal limit.

20. A system as recited in claim 18 wherein said operator means includes means for clamping the suture.

* * * * *